US007501301B2

(12) United States Patent  (10) Patent No.: US 7,501,301 B2
Kovacs et al. (45) Date of Patent: Mar. 10, 2009

(54) LOW COST FABRICATION OF MICROELECTRODE ARRAYS FOR CELL-BASED BIOSENSORS AND DRUG DISCOVERY METHODS

(75) Inventors: Gregory T. A. Kovacs, Palo Alto, CA (US); Laurent Giovangrandi, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 153 days.

(21) Appl. No.: 11/078,904

(22) Filed: Mar. 10, 2005

(65) Prior Publication Data

US 2006/0057771 A1 Mar. 16, 2006

Related U.S. Application Data

(60) Provisional application No. 60/552,320, filed on Mar. 10, 2004.

(51) Int. Cl.
*H01L 21/00* (2006.01)
(52) U.S. Cl. .................... 438/49; 204/403.01
(58) Field of Classification Search ............ 438/1, 438/22, 23–29, 106, 48, 49; 204/421, 403.01, 204/193, 194, 400, 412; 73/1.15; 422/82.01
See application file for complete search history.

(56) References Cited

U.S. PATENT DOCUMENTS

| 4,461,304 | A |   | 7/1984 | Kuperstein | 128/642 |
| 5,120,421 | A |   | 6/1992 | Glass et al. | 204/406 |
| 5,296,125 | A |   | 3/1994 | Glass et al. | 204/153.21 |
| 5,314,495 | A |   | 5/1994 | Kovacs | 623/25 |
| 5,378,343 | A | * | 1/1995 | Kounaves et al. | 204/413 |
| 5,425,869 | A |   | 6/1995 | Noding et al. | 204/418 |
| 5,432,086 | A |   | 7/1995 | Franzl et al. | 435/291 |
| 5,670,031 | A |   | 9/1997 | Hintsche et al. | 204/412 |
| 5,759,846 | A |   | 6/1998 | Stoppini et al. | 435/284.1 |

(Continued)

FOREIGN PATENT DOCUMENTS

WO   WO 2004/067734   8/2004

OTHER PUBLICATIONS

H, Sorribas et al. "Extracellular Stimulation of Neurons Cultured on Microelectrode Arrays" Laboratory for Micro and Nanotechnology, Paul Scherry Instute, CH-5232 Villgen PSI, PSI Annual Scientific Report, 2000, 1 page.

(Continued)

*Primary Examiner*—Brook Kebede
(74) *Attorney, Agent, or Firm*—Lumen Patent Firm

(57) ABSTRACT

A method for making a plurality of low-cost microelectrode arrays (MEAs) on one substrate utilizing certain unmodified printed circuit board (PCB) fabrication processes and selected materials. In some embodiments, a MEA device is composed of a thin polymer substrate containing patterned conductive traces. Coverlays on both sides of the substrate insulate the conductive traces and defines the electrodes. Preferably, flexible PCB technology is utilized to simultaneously define the microelectrode arrays. In an embodiment, the sensor is an integrated temperature sensor/heater in which the MEA device operates to record extracellular electrical signals from electrically active cell cultures. The present invention enables economical and efficient mass production of MEA devices, making them particularly suitable for disposable applications such as drug discovery, biosensors, etc.

27 Claims, 13 Drawing Sheets

U.S. PATENT DOCUMENTS

| | | | | |
|---|---|---|---|---|
| 5,810,725 | A | 9/1998 | Sugihara et al. | 600/372 |
| 5,981,268 | A | 11/1999 | Kovacs et al. | 435/287.1 |
| 6,024,702 | A | 2/2000 | Iversen | 600/378 |
| 6,032,062 | A | 2/2000 | Nisch | 600/372 |
| 6,051,422 | A | 4/2000 | Kovacs et al. | 435/287.1 |
| 6,130,056 | A | 10/2000 | Correges | 435/29 |
| 6,132,683 | A * | 10/2000 | Sugihara et al. | 422/82.01 |
| 6,151,519 | A | 11/2000 | Sugihara et al. | 600/372 |
| 6,235,520 | B1 | 5/2001 | Malin et al. | 435/287.1 |
| 6,254,827 | B1 | 7/2001 | Ackley et al. | 422/68.1 |
| 6,448,089 | B1 | 9/2002 | Vuong | 436/164 |
| RE37,977 | E | 2/2003 | Sugihara et al. | 422/82.01 |
| 6,586,257 | B1 | 7/2003 | Vuong | 436/165 |
| 6,638,483 | B2 | 10/2003 | Vuong | 422/82.05 |
| RE38,323 | E | 11/2003 | Sugihara et al. | 435/287.1 |
| 6,686,193 | B2 | 2/2004 | Maher et al. | 435/285.2 |
| 6,730,199 | B1 | 5/2004 | Hanni et al. | 204/403.02 |
| 6,758,961 | B1 | 7/2004 | Vogel et al. | 205/777.5 |
| 6,811,663 | B1 | 11/2004 | Freeman et al. | 204/400 |
| 6,814,933 | B2 | 11/2004 | Vuong | 422/82.05 |
| 6,829,498 | B2 | 12/2004 | Kipke et al. | 600/378 |
| 6,852,525 | B1 | 2/2005 | Cantor | 435/288.3 |
| 2004/0194302 | A1 | 10/2004 | Bhullar et al. | 29/847 |
| 2005/0023137 | A1 | 2/2005 | Bhullar et al. | 204/403.1 |

OTHER PUBLICATIONS

Smart Microsystems Products List from Windsor Scientific Ltd. of The United Kingdom, 2 Pages. Unknown Date.

MEA Technical Specifications, Copyright 2003 Multi Channel Systems MCS Gmbh, Date of Print Jan. 27, 2005 [Retrieved from the Internet on Mar. 8, 2005<URL:http://www.multichannelsystems.com/products/datasheets/sheetsintro.hym>, 1 page.

MEA systems Extracellular Recording with Microelectrode Arrays, Product Brochure,Copyright 2004 Multi Channel Systems MCS Gmbll [Retrieved from the Internet on Mar. 8, 2005<URL: http//www.multichannelsystems.com/products/measystem/measystemintro.htm>] 6 Pages.

Thomas Meyer et al. "Micro-Electrode Arrays in Cardiac Safety Pharmacology" Drug Safety 2004: 27 (11) ,, pp. 763-772.

Thomas Meyer et al QT- Screen: High- Throughput Cardiac Safety Pharmacology by Development Technologies, V. 2 No. 5,2004, pp. 507-514.

ecoMeasMulti Channel Systems MCS GmBH, Retrieved from the Internet on Mar. 8, 2005 <URL:http//www.multichannelsystems.com/prodoucts/meaprobes/meatypes/econmeas.htm>] 1 Page.

T. Meyer et al "Higher Throughput and Lower Costs in MEA Technology" Abstract, Technology Parc Tubingen/Reutlingen, Germany, Jul. 6-9, 2004, 1 page.

* cited by examiner

Top    Bottom (a) Single electrode per hole (b) Multiple electrodes per hole

Cross-sectional view | Top view (a) Coverlay with patterned metal lines (b) Coverlay with drilled holes through metal lines (c) Patterned overlay laminated onto substrate (d) Finished structure (vertical electrodes on the sides of the hole)

Electrodes on the sides

1) Multiwell plate format, non-communicating wells

2) Multiwell plate format with communicating wells a) Shared media state (high media level, common chemical and environmental conditions)

b) isolated well state (lowered media level, electrically and chemically isolated)

5 cm

LOW COST FABRICATION OF MICROELECTRODE ARRAYS FOR CELL-BASED BIOSENSORS AND DRUG DISCOVERY METHODS

CROSS-REFERENCE TO RELATED APPLICATIONS

This invention claims priority from the provisional patent application No. 60/552,320, filed Mar. 10, 2004, the entire content of which is incorporated herein by reference.

STATEMENT REGARDING FEDERALLY SPONSORED RESEARCH OR DEVELOPMENT

This invention was supported in part by the Defense Advanced Research Projects Agency (DARPA) under grant number N66001-99-C-8642. The U.S. Government may have certain rights in the invention.

FIELD OF THE INVENTION

This invention relates generally to microelectrode arrays and methods of making the same. More particularly, it relates to a printed-circuit-board (PCB) based method of fabricating low-cost microelectrode arrays useful for disposable applications such as cell-based biosensors, drug discovery, etc

BACKGROUND AND SUMMARY OF THE INVENTION

As one skilled in the art will appreciate, there has been a long felt need to substantially reduce the cost of fabricating microelectrode arrays (MEAs) for cell-based biosensors, etc. The present invention provides a method to fabricate low-cost microelectrode arrays and corresponding circuitry. More specifically, the present invention takes advantage of printed circuit board (PCB) fabrication technology to enable the efficient mass production of low-cost microelectrode arrays.

A key of the present invention is the discovery that certain unmodified PCB processes, combined with selective materials, can be utilized to mass-produce microelectrode arrays suitable for biological applications. As an example, sixty-electrode arrays can be simultaneously fabricated on one substrate.

PCB materials and fabrication processes are commonly used to produce computer motherboards and the likes. Conventional PCBs are not suitable for biological applications because many standard materials and processes have poor biocompatibility. In particular, standard, unmodified PCB fabrication technology is not generally known to be useful or viable for fabricating microelectrode arrays for recording extracellular electrical signals from electrically active cell cultures.

A conventional PCB is made of conductive wires (traces) "printed" or otherwise attached to a sheet of insulator (substrate). The PCB substrate is typically made of a phenol formaldehyde resin or a fiberglass-reinforced epoxy composite material.

There are three common PCB fabrication methods: photoengraving, PCB milling, and PCB printing. Although a conventional PCB can be made by adding traces to the substrate, the vast majority of conventional PCBs are manufactured by gluing a layer of copper foil over the entire PCB substrate, sometimes on both sides, then removing unwanted copper, leaving only the copper traces. A conventional PCB can also be made with a trace layer inside, producing a multi-layer PCB. After a conventional PCB is manufactured, components are typically attached to the traces by soldering.

U.S. Pat. No. 6,024,702, issued to Iversen and entitled, "IMPLANTABLE ELECTRODE MANUFACTURED WITH FLEXIBLE PRINTED CIRCUIT," discloses an implantable cylindrical electrode for monitoring tissue electrical activity and for tissue electrical stimulation. Iversen's implantable electrode is made with a printed circuit etched onto a flexible, non-conducting backing material of mylar or silicone. This patent addresses the problem of recording brain electrical activity at epileptogenic foci, which may comprise thousands or tens of thousands of neurons. It does not address the problem of recording extracellular electrical signals from electrically active cell cultures in vitro.

The extracellular electrical recording of electrogenic cells cultured over microelectrode arrays (MEAs) is a technique used increasingly over the last decade. As a fundamental research tool, it has been shown to yield valuable information on neuronal network and cardiac tissue dynamics. Recent reviews in the relevant field provide numerous references and further illustrate the applications of microelectrode arrays in cell-based biosensors, drug discovery, and safety pharmacology.

Production of these microelectrode arrays has typically relied on thin-film technologies derived from the microelectronic manufacturing industry. These technologies enable high-resolution (electrodes smaller than 10 μm) and high-density arrays (typically 32 to 64 electrodes with spacing down to 100 μm). However, none of these technologies are truly standard, resulting in high processing costs.

Scalability is another issue, as the cost of the chips increases markedly with size, as do packaging costs with array element number. This is of particular importance for multi-well designs incorporating several arrays. Lastly, the current paradigm is to reuse MEAs multiple times, driven mainly by the cost of commercially available MEAs. In addition to concerns about degradation of the array and of its performance and cross-contamination between experiments, such recycling involves additional (and often underestimated) costs due to handling, cleaning, and inspection.

The present invention addresses the aforementioned problems with a fabrication method based on unmodified PCB technology for producing low-cost MEAs useful for many practical applications, especially disposable applications such as cell-based biosensors, drug discovery, etc.

According to the present invention, unmodified, carefully selected PCB fabrication processes are used to simultaneously fabricate a plurality of microelectrode arrays and sensors on a suitable substrate made of, for instance, polymer. Depending upon the design and/or application, the microelectrode arrays and sensors can be formed on one side or both sides of the substrate. The substrate accordingly contains patterned conductive traces on one side or both sides. In an embodiment, the sensor is an integrated temperature sensor/heater.

The integrated heater/sensor takes advantage of the thermal properties of the metal lines "printed" on the substrate. Heater or heating elements can be incorporated on the same substrate using metal (e.g., copper) traces with minimal line width, providing fast, low power, controlled heating of the substrate. Similarly, temperature sensors or sensing elements can be realized using metal traces with minimal line width, providing a direct and accurate measurement and control of the substrate temperature.

In a specific embodiment, both the microelectrode array and the integrated sensor/heater are centrally located within the overall dimensions or footprint of a PCB. Covering layers (coverlays or insulation layers) on both sides insulate the metal line and defines the electrodes. The locations of the MEAs and sensors are not to be construed as limiting. For example, the fabrication method according to the present invention can be used to fabricate a disposable cartridge that has a plurality of MEAs (e.g., an array of microelectrode arrays) and sensors. In this case, other arrangements are possible and the MEAs and sensors do not need to be centrally located within the overall dimensions of the cartridge.

Based on the principles disclosed herein, multiple sensors of various kinds can be integrated onto the substrate. As an example, an oxygen sensor structure comprising three gold-plated electrodes is defined using the standard, unmodified PCB fabrication process. A solid electrolyte and a passivation layer are then deposited and patterned on top of the oxygen sensor electrodes, by way of, for instance, screen-printing, spraying, or droplets dispensing methods. Other possible sensor or sensors might measure pH, glucose, dopamine, or use a variety of ion selective amperometric techniques well known in the art.

An embodiment of the present invention is particularly useful for recording extracellular electrical signals from electrically active cell cultures. Examples of electrically active cells include, but not limited to, cardiomyocytes, neurons, pancreatic cells, and the likes. In the case for cardiac myocyte cultures, the electrode detects a traveling wave resulting from the depolarization of multiple, synchronized cells in a syncytium. Non-electrically active cells can also be utilized for toxin detection, pharmaceutical screening and the like, but measuring impedance of the cells and medium using the MEA. Such methods are well-known in the art, see, for example, U.S. Pat. No. 5,981,268, issued to Kovacs et al. and entitled, "Hybrid Biosensors," disclosing cell-based biosensors including variants with genetically engineered cells; Borkholder, D. A., Maluf, N. I., and Kovacs, G. T. A., "Impedance Imaging for Hybrid Biosensor Applications," Proceedings, Solid-State Sensor and Actuator Workshop, Hilton Head, S.C., Jun. 3-6, 1996, pp. 156-160; C. R. Keese and I. Giaever, "A whole cell biosensor based on cell-substrate interactions," Annual Intl. Conf. IEEE Engineering in Medicine and Biology Society, 12, 2 (1990), pp. 500-501; C. R. Keese and I. Giaever, "A biosensor that monitors cell morphology with electrical fields," IEEE Engineering in Medicine and Biology, 13, 3 (1994), pp. 402-408; and C. Xiao and J. H. Luong, "On-line monitoring of cell growth and cytotoxicity using electric cell-substrate impedance sensing (ECIS)," Biotechnology Progress, 19, 3 (2003), pp. 1000-1005.

Still further objects and advantages of the present invention will become apparent to one skilled in the art upon reading and understanding the preferred embodiments described below with reference to the following drawings.

DETAILED DESCRIPTION OF PREFERRED EMBODIMENT(S)

Microelectrode arrays of the present invention are preferably fabricated using flexible PCB (flex-PCB) technologies. Compared with their rigid counterparts, epoxy-based PCB technologies, Flex-PCB technologies provide denser integration, with typical feature size of 3 to 4 mils (75 to 100 µm). High-end technologies enabling much smaller features are usually not advantageous for low-cost applications due to their associated higher fabrication cost, although they could still be employed for applications that require smaller electrodes.

Flex-PCB technologies primarily use polyimide (most common), polyester or liquid crystal polymer (LCP) as substrates, copper as conductors, photolithography, drilling and laser etching for patterning, and various metal finishes, including gold. In comparison to microelectronic manufacturing, these commercial PCB technologies have been optimized for larger circuits, lower resolution, and are highly standardized to achieve the low cost imposed by the high-volume markets. In that respect, PCB technologies offer an excellent alternative for the fabrication of low-cost, single-use MEAs targeting, for example, cardiac applications.

The present invention distinguishes from the numerous prior examples of flexible multielectrode arrays involving flexible, polyimide films as substrates and using custom, thin-film processes, and not commercial PCB technologies, see, e.g., M. Sandison et al. "Effective extra-cellular recording from vertebrate neurons in culture using a new type of microelectrode array," Journal of Neuroscience Methods, 114, 1 (2002), pp. 63-71. Another prior example is disclosed in "Construction of a very high-density extracellular electrode array," American Journal of Physiology—Heart & Circulatory Physiology, 279, 1 (2000), pp. H437-442, in which R. A. Malkin et al. proposed a high-density microelectrode probe for in vivo cardiac mapping using the cross-section of a 20-layer flexible circuit board compatible with standard manufacturing.

Figure 1:
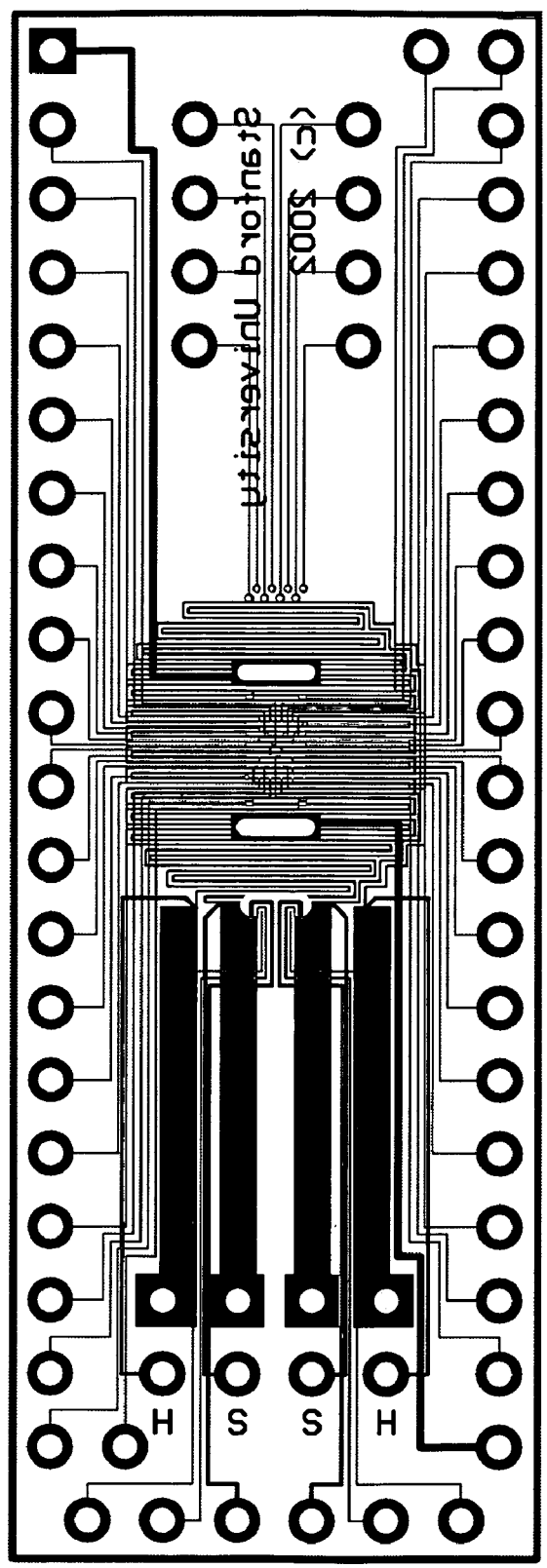
FIG. 1 is a top view of a printed circuit board (PCB) layout that schematically illustrates an embodiment of the present invention.

FIG. 1 shows a printed circuit board (PCB) layout embodying the present invention as if the substrate thereof is transparent. The substrate may be flexible or rigid. In some embodiments, the substrate is a thin polymer substrate containing patterned copper traces on both sides. Suitable substrates include polyimide, such as a polyimide under the trademark Kapton®, liquid crystal polymer, polyester, polyethylene naphtalate, and polytetrafluoroethylene, such as a tough, heat-resistant fluorocarbon resin under the trademark Teflon®.

In this embodiment, the microelectrode array design integrates 36 gold-plated, circular microelectrodes 75 or 100 μm in diameter on a 50 μm-thick Kapton® substrate (polyimide). These dimensions, while not the smallest achievable with flex-PCB technology, represent a desirable price/performance ratio. According to the present invention, the multi-layer feature of the PCB technology is used to integrate a heater and temperature sensor (based on the thermal coefficient of resistance of copper) using thin copper traces on the backside of the array, hence enabling temperature control of the active area.

In an article entitled, "Portable cell-based biosensor system using integrated CMOS cell-cartridges," Biosensors and Bioelectronics, 16, 7-8 (2001), pp. 543-556, B. D. DeBusschere et al. showed that it is possible to integrate on-chip thermal heating and sensing using CMOS technology. While this approach also enables integration of complex signal pre-processing and thermal management, it leads to expensive MEAs with the same issue of scalability discussed above. In contrast, using unmodified PCB technology, this embodiment enables on-chip heating at a minimal added cost.

The exemplary array layout was designed with the PCB design software Protel (Altium, Frenchs Forest, Australia). The generated Gerber files were then sent to PFC Flexible Circuits Limited (Scarborough, Ontario, Canada) for fabrication in a standard, unmodified two-layer polyimide technology. Specifications of the technology are given below for the purpose of exemplifying the invention and not to be construed as limiting. For clarity, dimensions related to the PCB are given in the industry standard, English units, doubled with metric units when necessary (note: 1 mil≈25 μm).

Figure 2:
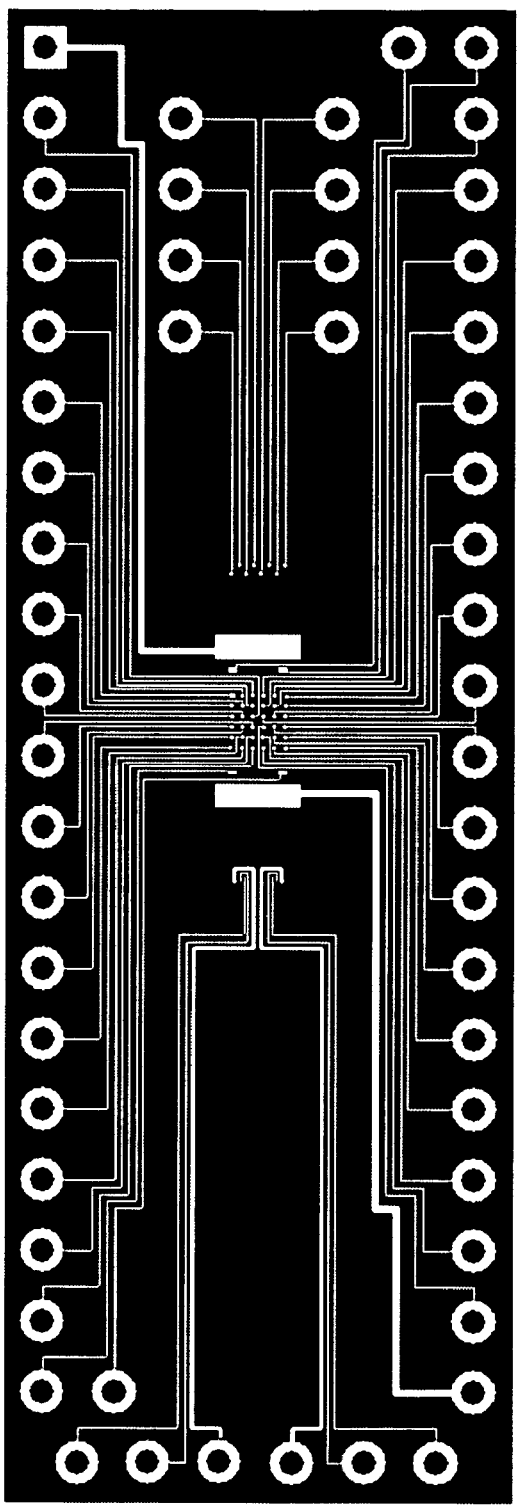
FIG. 2 exemplifies the top side and the bottom side of the PCB shown in FIG. 1.
Figure 2:
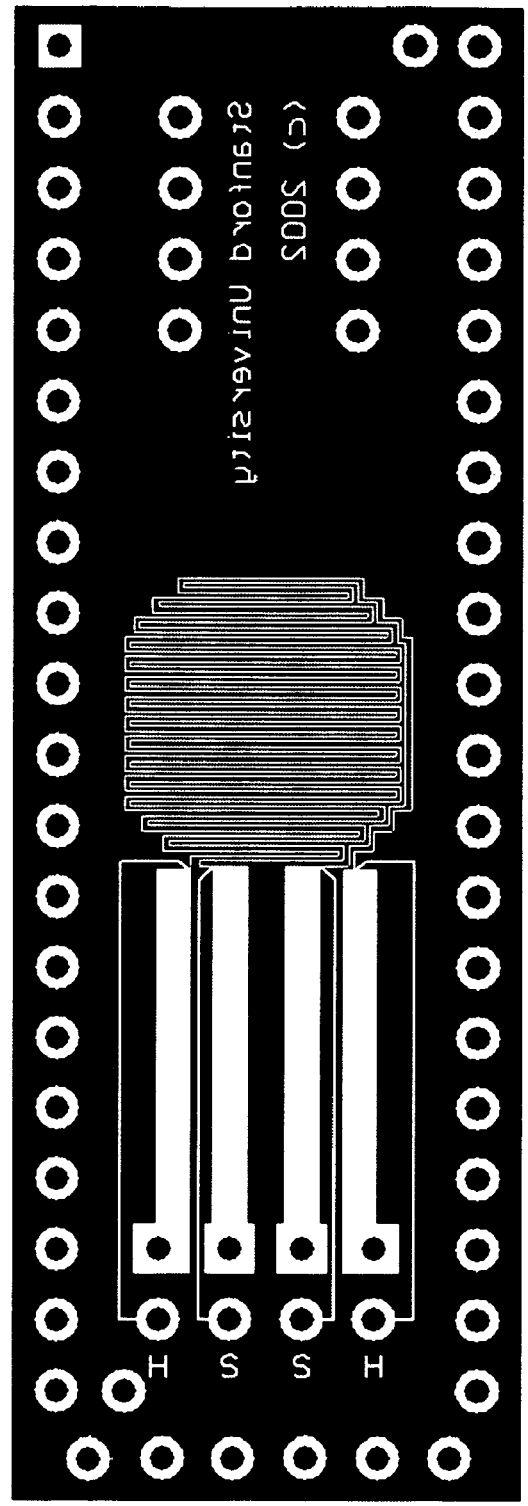

FIG. 2 shows both the top and bottom sides of an actual PCB embodying the present invention. In this exemplary embodiment, the substrate is an adhesiveless, 2-mil Kapton® film (Pyralux® series, DuPont™, Wilmington, Del.) with 0.5 oz/ft$^2$ (equivalent to a thickness of 18 μm) copper layers on each side. The 1-mil thick coverlays (Pyralux® series) are comprised of 0.5 mil of an acrylic adhesive and 0.5 mil of Kapton®. Openings of 3 and 4 mils are laser-etched. Larger openings are drilled. The exposed copper is coated with 100 to 150 microinches (2.5 to 3.8 μm) of electroless nickel and 3 to 8 microinches (75 to 200 μm) of gold (Type III, grade A, >99.9% purity).

Minimal line width and spacing imposed by the selected, unmodified PCB technology are 3 and 4 mils, respectively, enabling an interelectrode spacing of 380 μm. Thirty-six electrodes of either 3 mils (75 μm) or 4 mils (100 μm) were defined, covering a total area of 2×2 mm. In addition, two large reference electrodes were defined on opposite sides of the electrode array. An integrated temperature sensor and heater was defined on the backside of the circuit by two interlaced copper traces using a minimum line width of 3 mils. The dense folding (air gap of 4 mils) enabled a trace length of 28 cm within a circular area of 1 cm diameter under the electrode area. With a copper thickness of 18 μm, the traces had a theoretical resistance of about 3.5 ohms.

Figure 3:
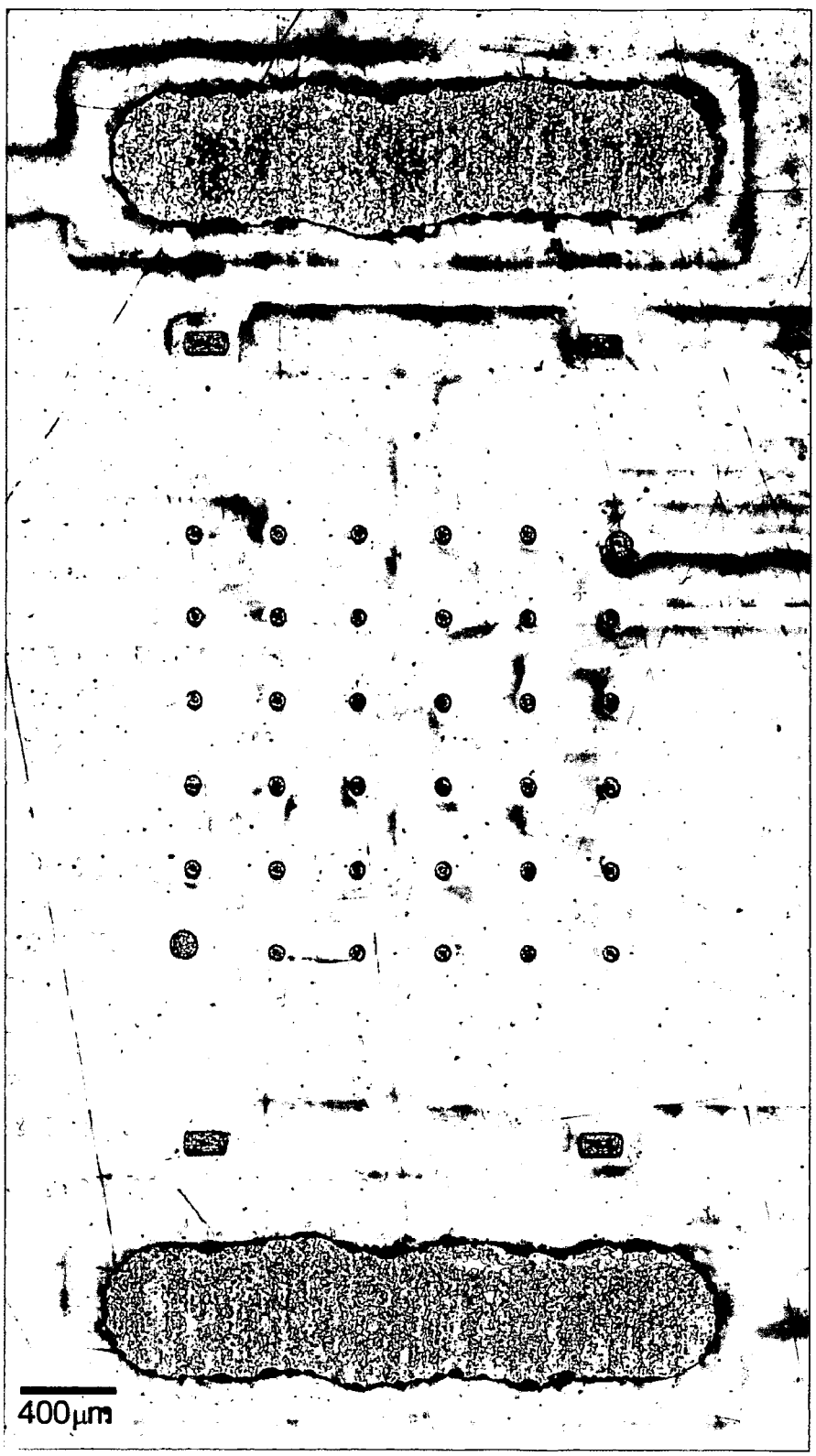
FIG. 3 is a photograph showing an exploded view of the active area of a microelectrode array according to an embodiment of the present invention.

FIG. 3 is a micrograph showing the active area of a microelectrode array according to the present invention. The size of the electrode may vary between 50-100 μm, depending on the type of substrate and/or application desired. The PCB industry is constantly trying to reduce the minimum feature size, so feature sizes are expected to be less than 50 μm, for instance, in the range of 10 μm.

Figure 4:
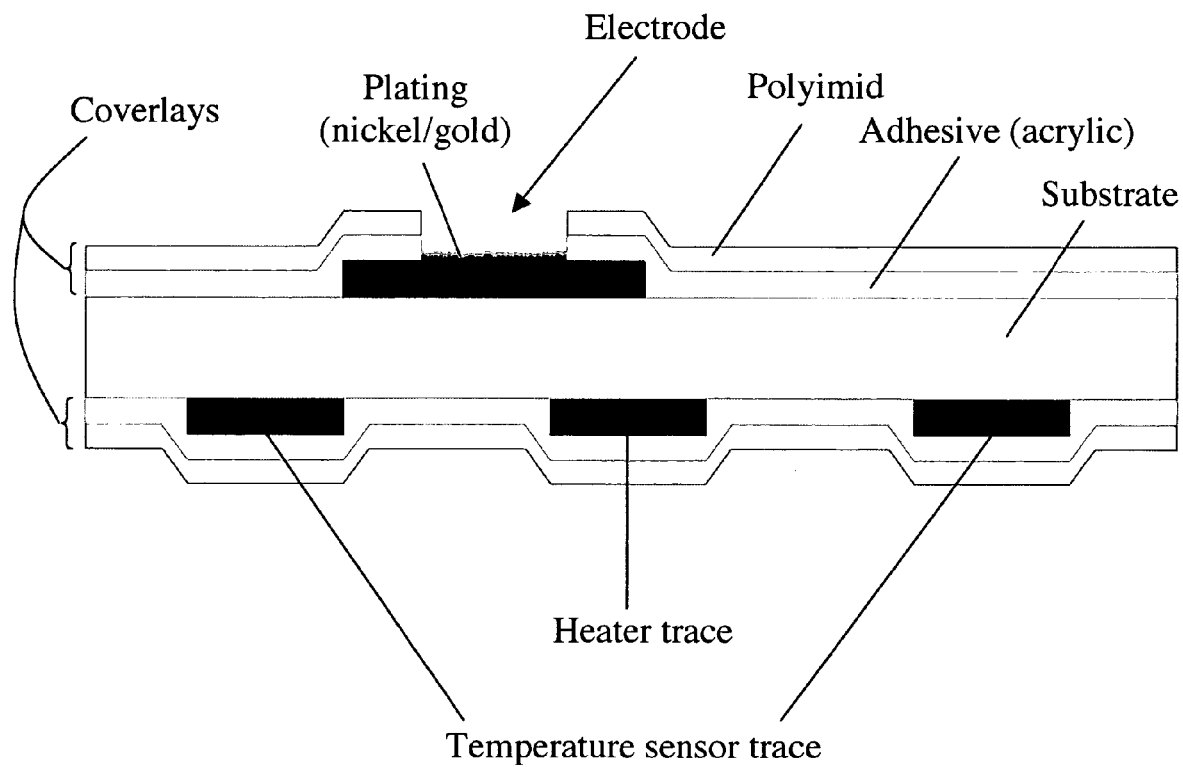
FIG. 4 is a cross-sectional view showing an embodiment of the present invention.

FIG. 4 is a cross-section structural view of an enlarged portion of an embodiment of the present invention. Covering layers (coverlays or insulation layers) on both sides insulate the metal line and define the electrodes. In this embodiment, the coverlay is made of polyimide material. Each polyimide coverlay is about 1 mil and the substrate is about 2 mils. In this embodiment, the overall dimension of the PCB is 2.1-inch× 1.5-inch with a total thickness of approximately 4-mil.

In a specific embodiment, the total thickness is a result of the two-layer PCB fabrication process with 0.5 oz/ft$^2$ copper, 2-mil polyimide substrate, and 1-mil coverlay. The copper traces have a 0.7-mil thickness. The thin circuit board according to the present invention has the advantages of fast time response and lower power dissipation than for a thicker substrate.

The circuits, flexible or not, can be built of mixed layers, such as FR-4 substrate and polyimide coverlays, to obtain desired chemical, mechanical, and/or biomechanical properties. In addition, multiple metal layers, possibly interconnected, can be integrated therein to provide additional features and to increase routing density. Moreover, the conductive material can also be different for each layer, providing even more flexibility in designing integrated heaters, temperature sensors, pH electrodes, oxygen sensors, or other integrated sensors/actuators.

The electrodes can be defined, arranged or otherwise configured in many ways. For example,
1) small electrodes might be defined by laser etching or plasma etching of the coverlay;
2) they can be defined by using copper lines of the smallest line width crossed by perpendicular openings in the top insulation layer using the smaller line width;
3) the adhesive flow (or thermal reflow) resulting the melting of the adhesive layer between the substrate and the coverlay can be used to reduce the effective opening in the coverlay, thereby producing electrodes smaller than the initial hole in the coverlay;
4) small electrodes can be defined using a large opening in the coverlay that reveals only the tip of a minimal width metal line, thus greatly relaxing the requirements on the minimal feature to be defined in the coverlay; and
5) small, vertical electrodes can be produced using the cross-section of a minimal width metal line. Such an electrode could be defined by drilling a hole through metal lines deposited on the coverlay, and subsequent lamination to a substrate. This would define vertical electrodes at the bottom and periphery of the hole, yet providing intimate contact with cells or other biological tissue. The electrode size is then defined by the cross-section of the metal line.

Figure 5:
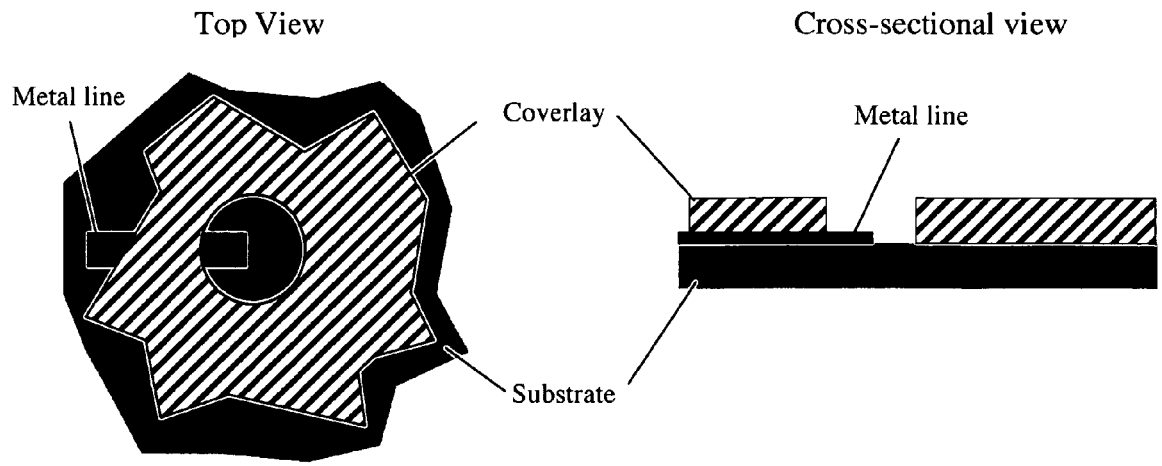
FIG. 5 shows small electrodes defined using a minimal width metal line and a relatively large overlapping, off-centered hole in the coverlay.
Figure 5:
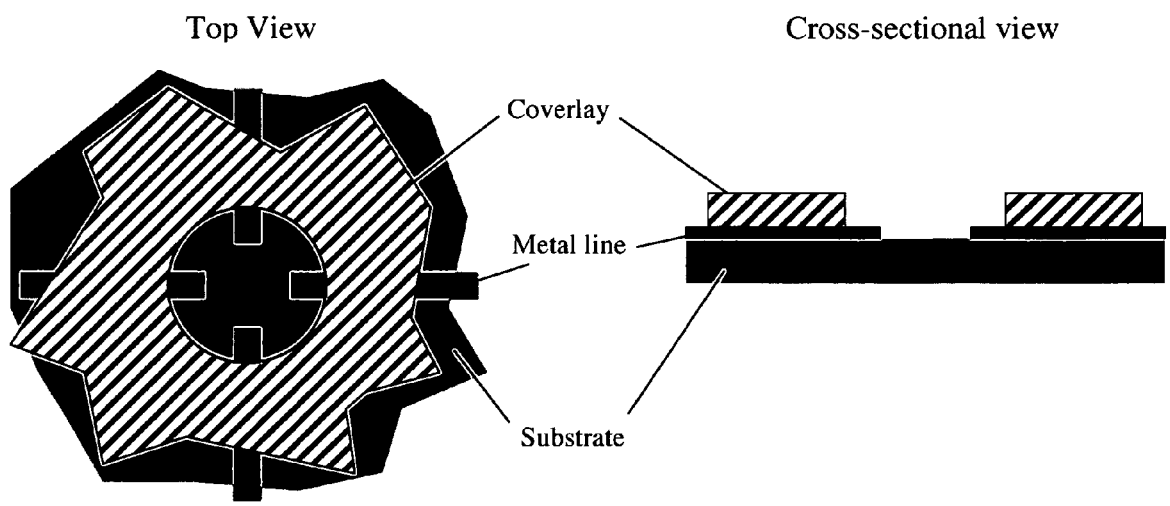
Figure 6:
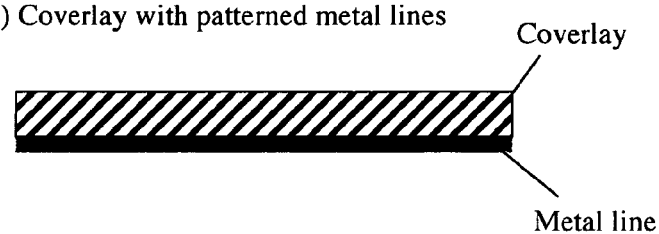
FIG. 6 shows small, vertical electrodes using the section of a small width metal line.
Figure 6:
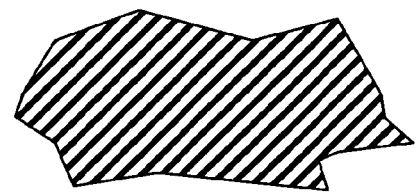
Figure 6:
Figure 6:
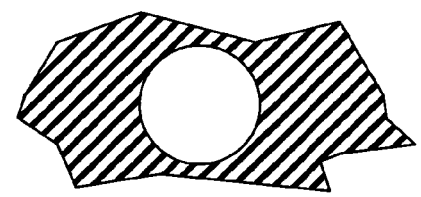
Figure 6:
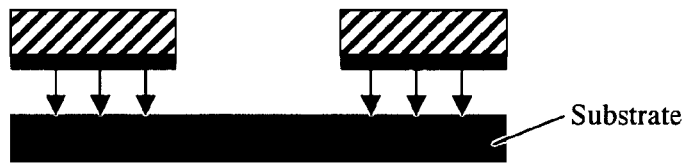
Figure 6:
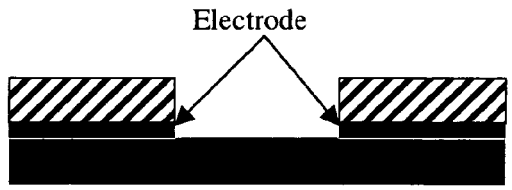
Figure 6:
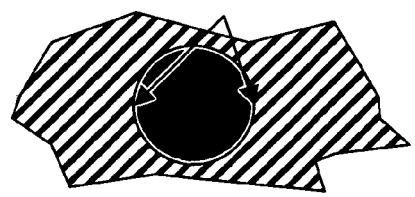

The latter two arrangements allow multiple electrodes to be defined with a single large hole, with the metal lines being exposed at the periphery of the hole. FIGS. 5-6 exemplify these arrangements. FIG. 5 shows small electrodes defined using a minimal width metal line and a relatively large overlapping, off-centered hole in the coverlay. The minimal electrode size is thus defined only by the minimal line width achievable in the technology, and the overlap between the tip of the metal line and the hole in the coverlay. FIG. 5(a) shows a single electrode configuration (one electrode for each hole), FIG. 5(b) shows a multiple electrode configuration (one large hole simultaneously defines multiple electrodes). FIG. 6 shows small, vertical electrodes using the section of a small width metal line. The electrode size can be varied using the line width and the metal layer thickness. The electrodes are plated with a suitable coating such as gold, platinum, iridium, Ag/AgCl$_2$, etc. so to confer necessary properties for electrical recording or stimulation of the cells.

Controlled heating of the substrate/microelectrode array is achieved by the integrated heater/sensor that takes advantage of the thermal properties of the metal lines. In a specific embodiment, heating elements are incorporated on a thin substrate using metal (e.g., copper) coils with minimal line width. Because of the low thermal mass of the thin substrate, such an arrangement provides a fast and low-power heating of the substrate. Similarly, temperature sensing elements can be realized using copper traces with minimal line width, providing a direct and accurate measurement of the substrate temperature.

The temperature sensing elements or sensor traces, used as resistive temperature detectors (RTDs), were characterized for resistance and thermal coefficient (TCR) variability, as well as for drift over time in culture conditions. Drift under culture conditions was characterized after 8 and 39 days. The substrates were stored immersed in PBS at 37° C. A full calibration of the temperature sense traces was then performed. Results showed no significant drift of either the nominal resistance or the TCR over the tested period.

The use of the copper layer of an unmodified PCB process for the integration of a heater, and in particular a temperature sensor, is subject to several conditions, including the stability of the thermal (TCR) and electrical properties (nominal resistance) over time, and to a lesser extent the reproducibility of these properties between arrays. Stability over time is key to allow for a single initial calibration, used over the entire course of the experiment. Reproducibility across chips would remove the need for individual calibration. Results show that both the nominal resistance and the TCR are stable. However, the spread of the nominal resistance across chips (±5.4%) translates into an absolute error of ±1.26° C. at 37° C. (using a TCR of 0.403%/° C.). On the other hand, the TCR shows a much better stability across chips (±1.7%), which translates into an absolute error of only ±0.21° C. at 37° C. (using a nominal resistance of 3.91 Ω).

A single-point calibration determines the nominal resistance and thus reduces the absolute temperature error to the single TCR error, which is less than ±0.25° C. over the useful range of 25 to 40° C. The choice of the calibration method is dependent on the requirements of a specific application. These results show that a single-point calibration of the integrated copper resistors leads to performance that should suit most cell-based applications.

The manufactured MEAs have been characterized both electrically and functionally. Electrical characterization included electrode impedance measurements, temperature sensor variability across MEAs and stability over time. Functional tests have been conducted with HL-1 cardiomyocyte cultures (see, e.g., FIGS. 11-13). The HL-1 cell line, derived from mouse atrial myocytes, has been extensively characterized on standard, glass microelectrode arrays, with regard to both biochemical and environmental sensitivity. Relevant teachings regarding the HL-1 cell line and its biochemical and environmental sensitivity can be found in the following papers, which are incorporated herein by reference:
1. W. C. Claycomb et al. "HL-1 cells: a cardiac muscle cell line that contracts and retains phenotypic characteristics of the adult cardiomyocyte," Proceedings, National Academy of Sciences of the United States of America, 95, 6 (1998), pp. 2979-2984.
2. K. H. Gilchrist et al. "Analysis of microelectrode-recorded signals from a cardiac cell line as a tool for pharmaceutical screening," Transducers '01—Eurosensors XV, Munich, Germany, 2001.
3. K. H. Gilchrist et al. "Sensitivity of cell-based biosensors to environmental variables," Biosensors and Bioelectronics, 20, 7 (2005), pp. 1397-1406.

Based on the principles disclosed herein, multiple sensors of various kinds can be integrated onto the device. As an example, an oxygen sensor structure comprising three gold-plated electrodes is defined using carefully selected standard (unmodified) PCB fabrication methods. A solid electrolyte and a passivation layer are then deposited and patterned on top of the oxygen sensor electrodes, by way of, for instance, screen-printing, spraying, or droplets dispensing methods. Other possible sensors might include pH, glucose, dopamine, ion selective amperometric sensors.

With the same PCB fabrication process, small culture wells can be integrated directly onto the substrate, enabling a high density of wells on a single substrate. This can be achieved by using thick coverlays, e.g., more than 50 μm, molded, stamped or drilled to define wells or micro-wells before their lamination on the substrate. In some embodiments, these micro-wells share a common culture medium, enabling simultaneous experiments on electrically and physically independent cultures.

Alternatively, they have non-connecting culture medium, enabling simultaneous experiments on electrically, physically, and chemically independent cultures. By flooding with medium and fluidically connecting the wells, or draining the overlying medium to isolate them for independent measurements, it is possible to transition between the isolated and non-isolated well states at will. This latter mode is particularly suited to disposable, multi-MEA cartridges. To prevent cells from growing on the top surface and connect or contaminate adjacent micro-wells, the top surface of the coverlay can be chemically modified using contact transfer.

Figure 7:
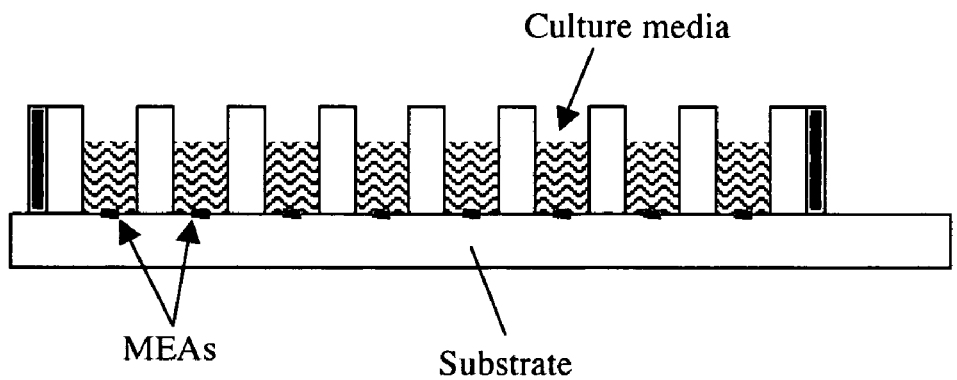
FIG. 7 illustrates multiple MEAs arranged in a multiwell plate format, with (1) non-commuting and (2) commuting wells.
Figure 7:
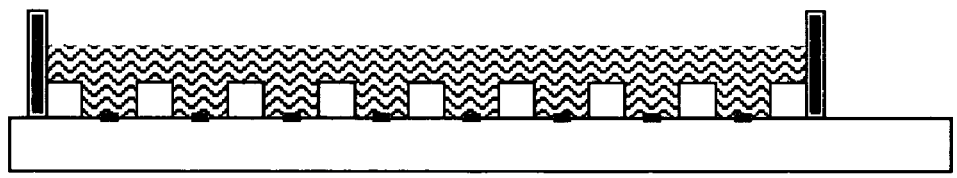
Figure 7:
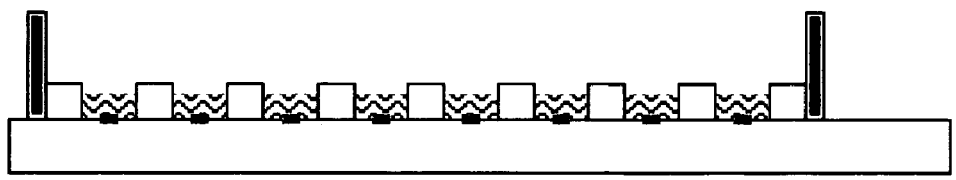

FIG. 7 illustrates multiple MEAs arranged in a multiwell plate format, with (1) non-commuting and (2) commuting wells. Standard, separated wells are isolated chemically and electrically. When the level of media is high, all wells are submerged and share a common media (typically for growth under identical conditions). When the media level is lowered, the wells become isolated, both chemically and electrically, and individual assays can be performed in each individual wells.

Figure 8:
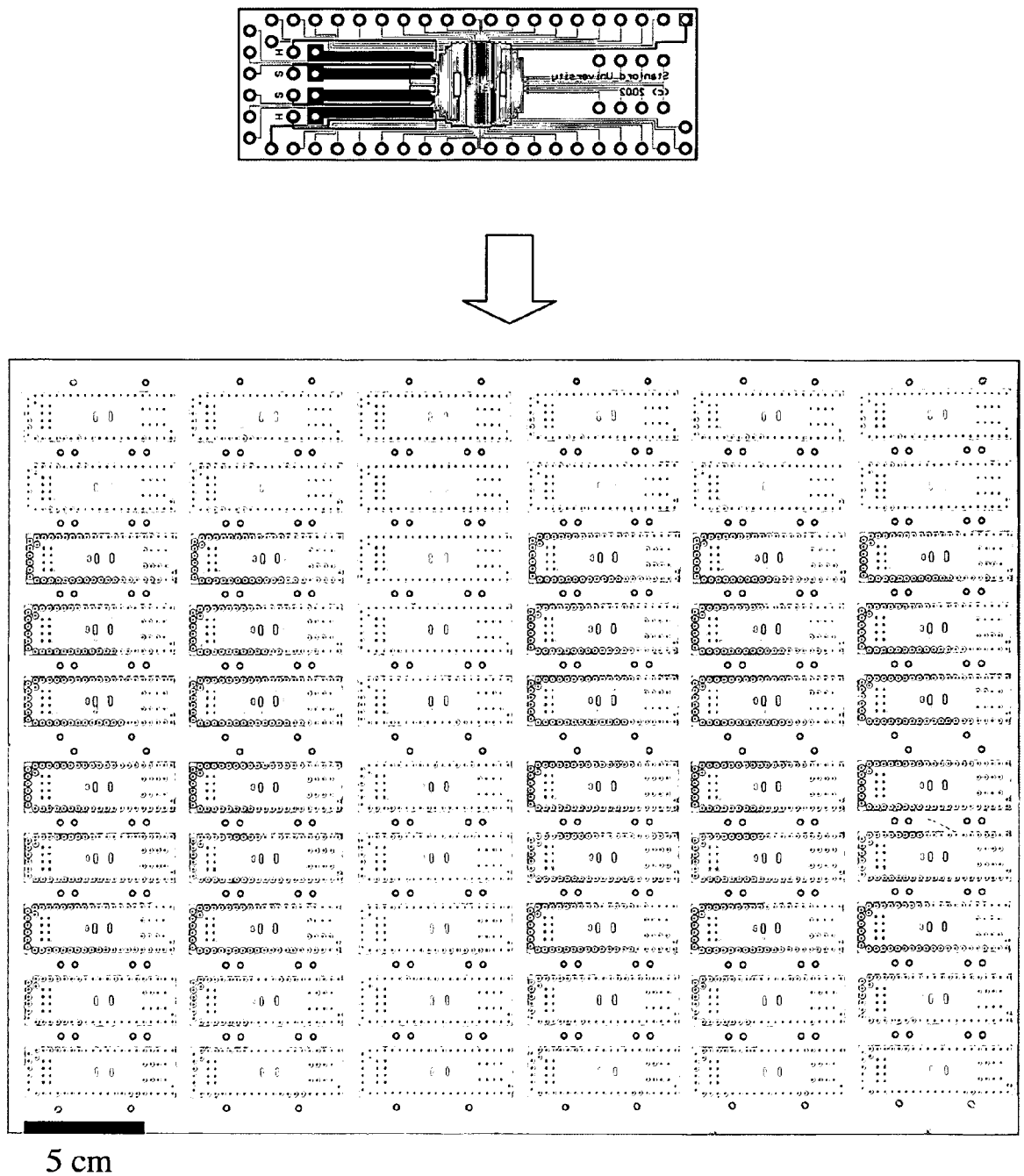
FIG. 8 exemplifies an embodiment of the present invention, producing 60 MEAs on the same substrate.

Utilizing the fabrication principles and materials described above, 60 MEA devices, each having a microelectrode array on the top side and an integrated sensor/heater on the bottom side, can be mass produced on one sheet of substrate, as shown in FIG. 8.

Figure 9:
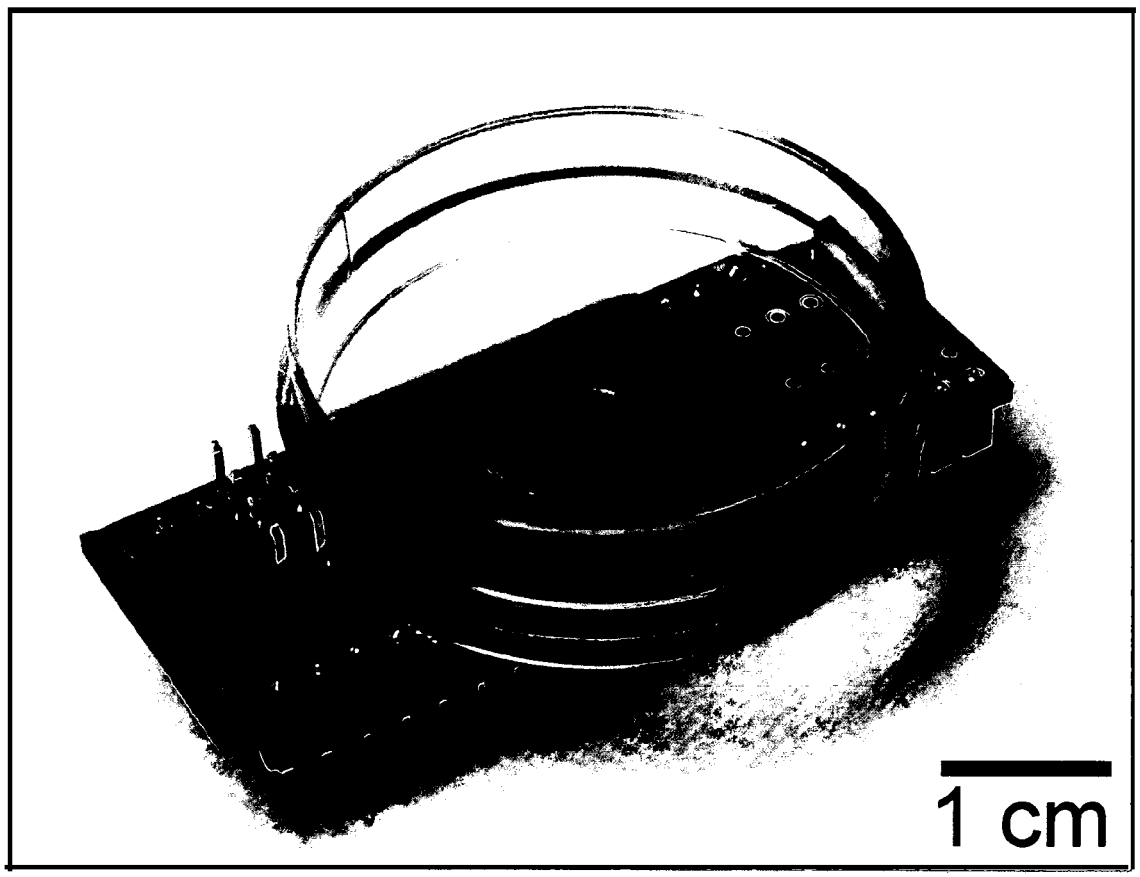
FIG. 9 is a photograph showing an exploded view of an embodiment of the present invention with a cell culture dish residing thereon.

FIG. 9 illustrates an example of the final integration of a MEA device. An assembled flex-MEA is mounted on a rigid substrate with connecting pins and attached to a cell culture dish. The two large electrodes (635×2800 μm) visible in the center of the circuit are used to ground the culture bath during recording. The bottom pins connect the recording electrodes, while the top pins connect the heater and temperature sensor traces.

Leveraging a standard, substantially unmodified PCB technology for a biological application such as the extracellular recording of electrically active cell cultures presents some major risks, most notably biocompatibility issues. This could arise from impure materials and contamination associated with the fabrication process, as well as from the properties of the materials in use.

PCB fabrication is, for the large part, not done in a cleanroom environment, and is thus more prone to external contamination. Also, the requirements on the material purity are less stringent than for clean-room processing. More specific to polyimide-based flexible circuits is the risk of potentially toxic copper ions leaching out through the polyimide, known for its high water absorption (2 to 3% for standard polyimide as used in some embodiments).

Of the 55 flex-MEAs tested to date, only two were found cytotoxic on their first use with HL-1 cells. This shows an apparent lack of systematic toxicity associated with the processing, as well as an inherent biocompatibility of the materials involved. It should be noted that the material biocompatibility is a result of careful pre-selection (data not shown) based on cell culture experiments with various types of PCB substrates.

For instance, standard FR4/LPI (liquid photo imageable coverlay) showed inconsistent results from batch to batch, possibly due to more process-dependent surface (UV illumination and curing will influence the final chemical composition). Regarding long-term cytotoxicity, flex-MEAs were routinely used for three to four cell platings (runs) lasting between seven and nine days each. Except for the two devices found toxic at the first cell plating, all the remaining devices supported cell growth for at least three runs (more than 21 days in culture), some extending up to six runs with successful electrical recording (38 days). The limiting factor appeared to be the catastrophic failure of the gold plating after three or more runs, with pieces of the gold plating lifting off from the large ground electrodes during the cleaning step. It should be noted that the cleaning itself might have contributed to the degradation of the circuits by mechanical (strong water rinse), or chemical (detergent with pH of 12) means.

These results demonstrate the suitability of polyimide-based flex-MEAs to support HL-1 cell growth over the typical culture life cycle of 7 to 10 days. In addition, the arrays were found to be reusable to a certain extent, increasing their life span to several weeks if necessary. Longer uses might also be possible by improving the electrode plating (notably by using thicker gold platings), or modifying the cleaning protocol.

Two batches of circuits, targeting electrodes with diameters of 100 µm (4 mils) and 75 µm (3 mils) respectively, were manufactured using the selected, substantially unmodified PCB technology. The first batch (100 µm target openings) had electrodes with a measured average diameter of 101.3±4.3 µm (mean±S.D., n=24). The second batch (75 µm target openings), reportedly under-etched, had electrodes with a measured average diameter of 65.2±1.8 µm (n=25). For accuracy, these will be referred to as 65 µm electrodes hereinafter. All electrodes were found to be recessed 15 to 20 µm below the surface, due to the thickness of the coverlay.

The manufactured flex-MEAs were cleaned with isopropyl alcohol and mounted on a rigid FR4 template. Single-in-line connectors were soldered to enable the electrical connection to a previously developed amplifier board via a zero-insertion-force (ZIF) socket. Finally, a 35-mm diameter Petri dish (Nalge Nunc International, Rochester, N.Y., USA) with a 10-mm diameter hole drilled in the bottom was glued (Supreme 42HT epoxy, Master Bond Inc., Hackensack, N.J., USA) on top to define the cell culture chamber. This is the final cartridge shown in FIG. 9. It should be noted that without the need to maintain compatibility with existing hardware, the design of the circuit can be greatly simplified to take advantage of card-edge connection systems, reducing the post-manufacturing assembly to simple gluing operations.

The MEA device fabricated according to the present invention can incorporate discrete electronic components such as amplifiers or multiplexers to increase noise performance and electrode/micro-well density. As one skilled in the art will appreciate, other on-chip electronic components can be readily integrated on the MEA device using techniques known in the art. The preferred assembly methods include flip-chip bonding or direct chip-on-board (COB) bonding.

Figure 10:
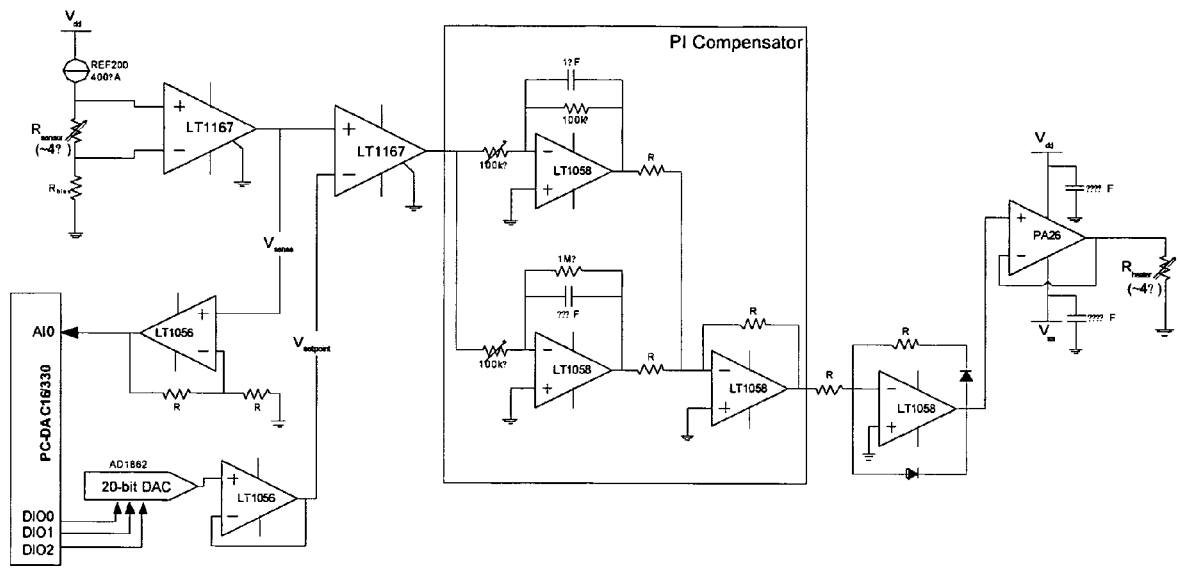
FIG. 10 is a block diagram schematically showing an embodiment of the present invention incorporating an analog Proportional-Integral (PI) controller for low noise, accurate temperature regulation.

FIG. 10 is a block diagram schematically showing an embodiment of the present invention incorporating an analog Proportional-Integral (PI) controller for low noise, accurate temperature regulation (±0.1° C.). Using the measured nominal resistance of the integrated temperature sensor traces, the flex-MEAs were used together with the PI controller to control the temperature of the substrate while simultaneously recording the electrical activity of the cells. PI controller is known in the art and thus is not further described herein for the sake of brevity. In some embodiments, a device fabricated according to the present invention is interfaced with a computer for set point programming and temperature logging. The PI controller and any other electronics could be integrated directly onto the device using the methods described above.

Figure 11:
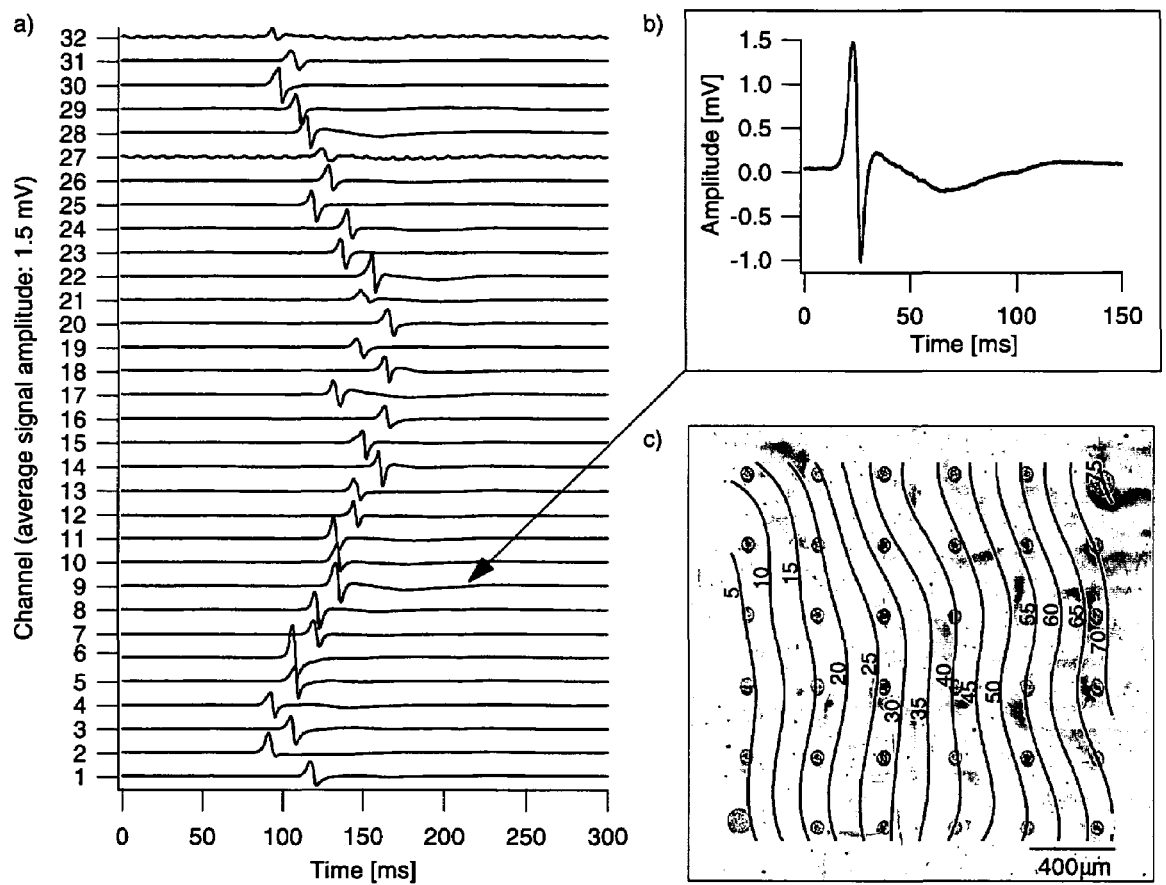
FIGS. 11-13 show that a MEA fabricated according to the present invention operates to record electrical signals from cardiac (HL-1) cells.
Figure 12:
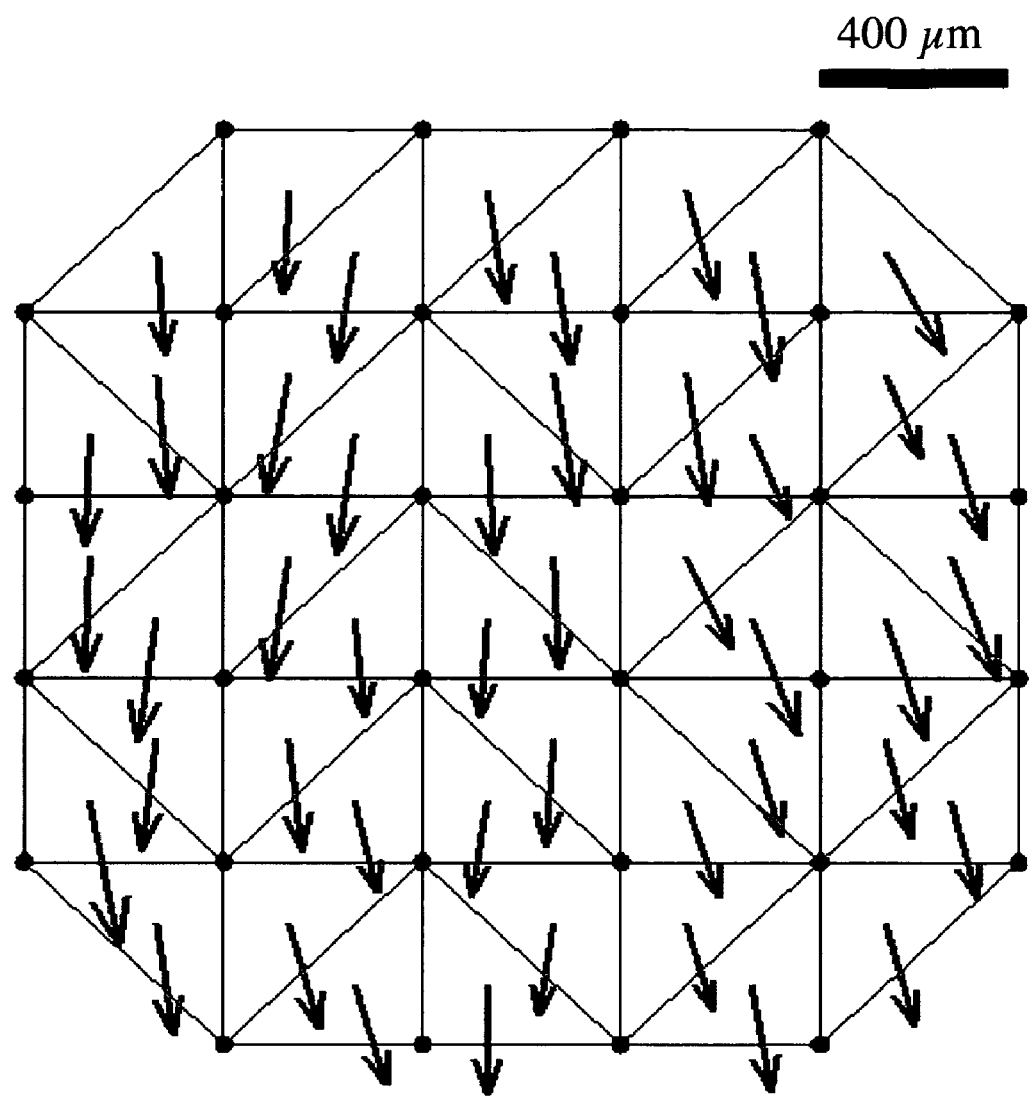
Figure 13:
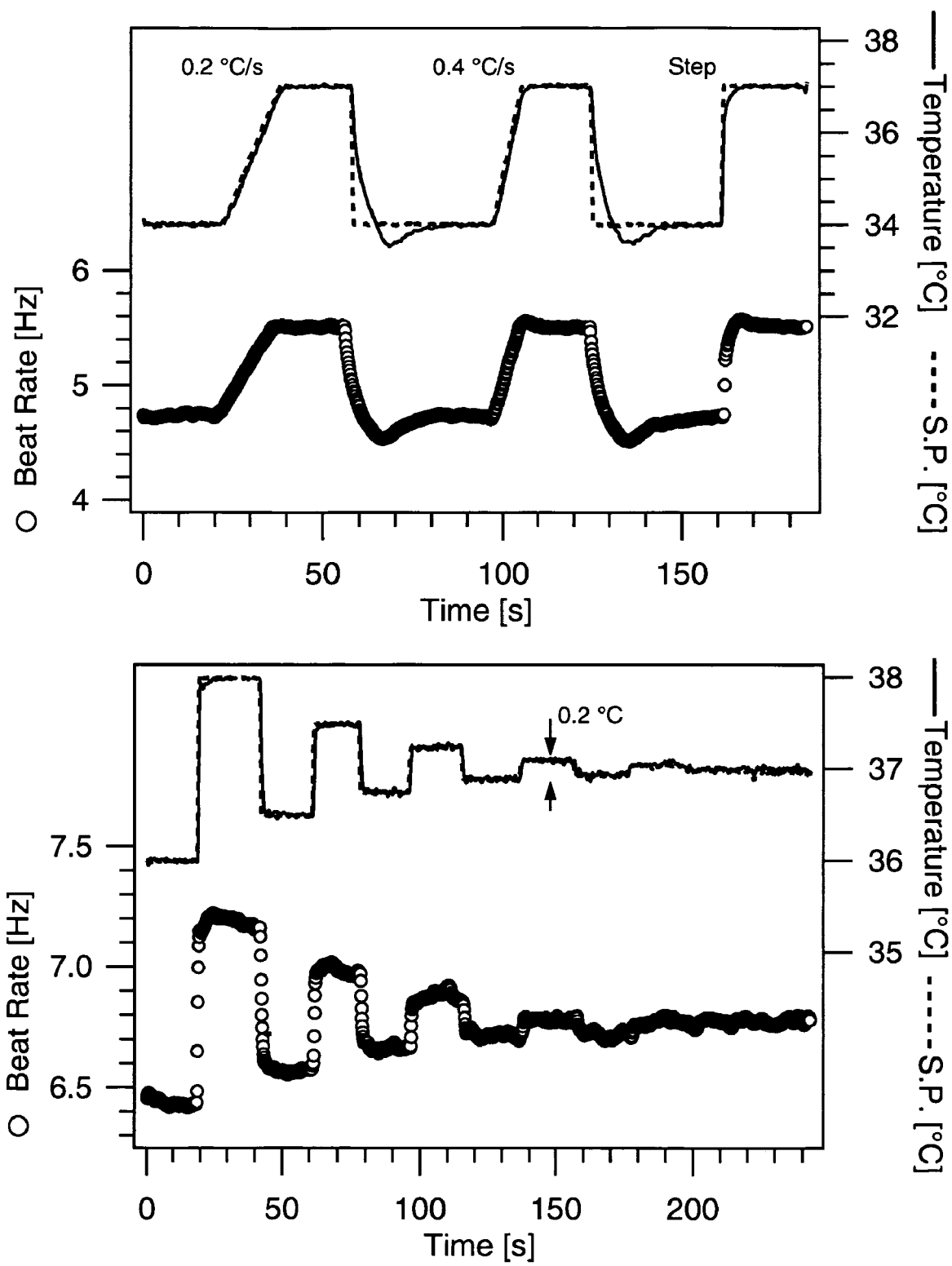

FIGS. 11-13 show that a MEA device fabricated according to the present invention operates to successfully record signals from microscopic cardiac (HL-1) cells cultured on the MEA. In this example, the MEA device has a MEA centrally located on the topside and an integrated temperature sensor/heater on the bottom side thereof. The techniques, tools, and environment necessary to grow, monitor, and analyze cardiac cells are generally described in the above-referenced articles by W. C. Claycomb et al. and K. H. Gilchrist et al.

FIG. 11 shows extracellular recording of HL-1 signals with a 100 µm electrode flex-MEA: a) 32-channel snapshot of a depolarization wave, b) close-up of an action potential showing the typical fast upstroke-downstroke followed by slower modulations, c) isochronal map interpolated from the local activation time (LAT), showing a homogeneous propagation of the depolarization wave across the array (isochrone timings are given in milliseconds). The corresponding conduction velocity is 2.7±0.4 cm/s (mean±S.D., n=40 triplets of electrodes). For reference, an image of the electrode area is superimposed on the map. FIG. 12 maps the wavefront propagation where the average conduction velocity reaches 2.7 cm/s. Small black dots represent the microelectrode array of the device.

Measurement of electrode impedance was conducted on a custom impedance analyzer by D. A. Borkholder et al., which is described in "Impedance imaging for hybrid biosensor applications," Solid-State Sensor and Actuator Workshop, Hilton Head Island, S.C., 1996, and which is incorporated herein by reference. Briefly, a 50 mV$_{p-p}$ AC voltage was used to drive the individual electrodes, and the resulting current (collected at the ground electrodes) was converted to a voltage, amplified, and separated into real and imaginary parts using a lock-in technique. The ground electrode's contribution to the measured impedance was negligible due to its large size compared to the individual electrodes (>500×). Known value resistors were used to calibrate the system. All measurements were conducted in phosphate buffered saline (PBS, 137 mM NaCl), after a 120-min hydration period.

The electrode impedance displayed an expected behavior for metal electrodes in saline/physiologic solution, with a typical frequency dependence of $f^{-\alpha}$ ($\alpha$=0.95) for the magnitude, and a phase roughly constant across the 0.5-5 kHz range. The magnitude at 1 kHz was 215.3±70.3 kΩ (mean±S.D., n=165) for 65 µm diameter electrodes, and 154.7±16.9 kΩ (n=165) for the 100 µm diameter electrodes. The phase at 1 kHz was −80.7±6.5° and −82.1±3.5°, for 65 µm and 100 µm diameter electrodes, respectively. The variation of electrode roughness associated with the plating process likely explains the spreading observed in the impedance magnitudes within batches. Nevertheless, it should be noted that these impedances are small enough to guarantee a low thermal noise level (under 2.5 µV$_{RMS}$ over a 10 kHz range for the 65 µm electrodes), thus eliminating the need for impedance reduction techniques such as platinum black electroplating.

It should be noted that for electrical impedance measurement of the cells themselves, the same approach can be used as is well-known in the art, see, e.g., Borkholder et al. "Impedance Imaging for Hybrid Biosensor Applications," supra; and U.S. Pat. No. 5,981,268. If cells are present, the impedance can be monitored to detect changes in the state of the cells that can indicated response to toxins or pharmaceuticals, aging, etc.

Extracellular signals were amplified and filtered with a custom 36-channel amplifier, which is described in detail by K. H. Gilchrist et al. in "General purpose, field-portable cell-based biosensor platform," Biosensors and Bioelectronics, 16, 7-8 (2001), pp. 557-564, which is incorporated herein by reference. The amplifier had a gain of 1000x, and a band-pass characteristic with corner frequencies of 4 Hz and 3 kHz for high- and low-pass, respectively. The amplified signals were digitized at 10 kHz. A thermal enclosure kept the MEA at a constant temperature (within 0.1° C.) when the on-chip heating capabilities were not used.

The flex-MEA temperature was controlled using a custom circuit. Temperature measurement of the substrate was achieved with a four-point measurement of the temperature sense trace. Sensitivity after amplification was 6.4 mV/° C., assuming a thermal coefficient of resistance (TCR) for copper of 0.4%. Temperature control was performed using a proportional-integral (PI) error-circuit driving the heating trace. The system was interfaced to a computer, enabling logging and programmatic modulation of the temperature (steps, ramps, etc.), based on calibrated TCR and resistance at 25° C. (see 2.5). Noise reduction in the temperature measurements was achieved using a moving average filter (500 ms).

Calibration of the integrated temperature sense traces was performed using a 6.5-digit multimeter (A34401A, Agilent, Palo Alto, Calif., USA) configured for four-wire measurement, and an external, calibrated temperature probe (type 554, YSI Inc., Yellow Springs, Ohio, USA) as reference. Measurement of resistance and temperature were simultaneously performed at steady state after complete temperature stabilization (10- to 15-min.). For full calibration (resistance at 25° C. and TCR), measurements were conducted at multiple temperatures, ranging from around 4° C. (in a refrigerator) to 40° C., using a small, regulated thermal enclosure. For single-point calibration, the resistance at room temperature was measured, and the nominal resistance, referred to 25° C., was calculated using an average TCR of 0.403%/° C.

FIG. 13 shows plots of the temperature step and ramp responses of HL-1 cells cultured on an assembled flex-MEA device with an integrated temperature sensor/heater. These experiments use the fast settling times resulting from the small thermal mass of the system to quickly change the temperature of the cell layer. The graphs show the temperature set point (S.P.), the actual temperature as measured by the temperature sense trace, and the beat rate of the HL-1 cells. Note how closely the beat rate follows the temperature profile: ramps generate linear increases; the step of 0.2° C. is still clearly visible in the beat rate; the correlation between the temperature steps and the beat rate steps in the bottom graph is better than 0.993.

Prior to seeding the cells, the microelectrode arrays were sterilized with 70% ethanol and coated with an adhesion-promoting solution containing 0.001% fibronectin (Sigma, St. Louis, Mo., USA) and 0.02% gelatin (BD Biosciences, Sparks, Md., USA) and stored in a 37° C. incubator overnight. A suspension of HL-1 cells in culture media was obtained from a confluent flask of cells. The culture medium consists of Claycomb media (JRH Biosciences, Lenexa, Kans., USA), supplemented with 10% fetal bovine serum (JRH Biosciences), 100 µM norepinephrine (Sigma), 100 units/ml penicillin-streptomycin (Invitrogen Corp., Carlsbad, Calif., USA), and 4 mM L-glutamine (Invitrogen). The gelatin/fibronectin solution was aspirated from the arrays and replaced with the cell suspension. The cells were plated at a density of approximately 1200 cells/mm$^2$. The cultures reached confluence and showed spontaneous electrical activity two days after plating. Electrical recordings were performed between day 2 and day 10 after plating.

For the evaluation of the stability of the temperature control and the resulting cellular response, a flow-through system and buffered medium were used to minimize osmolarity and pH variation. The flow-through setup consisted of a syringe pump (74900 Series, Cole Parmer Instrument Co., Vernon Hills, Ill., USA) pushing media at a rate of 100 µl/min into the cell chamber, and a peristaltic pump (P720, Instech Laboratories, Inc., Plymouth Meeting, Pa., USA) evacuating the media out of the chamber. This configuration allowed for smoother flow compared to a peristaltic-only pumping. The media was buffered with 20 mM HEPES (Sigma, St. Louis, Mo., USA), adjusted to pH 7.4 with NaOH.

The two plots of FIG. 13 show two experiments emphasizing the fast settling times resulting from the small thermal mass of the system. The top graph shows a series of computer-controlled ramps (0.2° C./s, 0.4° C./s) and steps between 34° C. and 37° C. The temperature measured by the temperature sense trace exhibits very rapid changes, with a settling time (to ±0.1° C.) of five seconds for the step and no overshoot. The temperature accuracy is better than 0.1° C. The power required to keep the temperature of the substrate at 37° C. was only about one watt (ambient temperature of 25° C.). The cooling time for the 3° C. step down to 34° C. is under 10 seconds. Note that the dip in the temperature following the decreasing steps is caused by the integral term of the analog PI compensator. The cell response is illustrated by the beat rate and strictly follows the temperature, alternating between 4.7 Hz at 34° C. and 5.5 Hz at 37° C. A slight overshoot in the beat rate is visible following the step, and to a lesser extent following the 0.4° C./s ramp. Similar results were obtained over five different cultures.

The bottom graph further illustrates the high sensitivity of HL-1 cells to temperature, showing 20-second temperature steps with decreasing amplitude (2° C. down to 0.05° C.). The beat rate variation again strictly follows the temperature variation, with a correlation coefficient better than 0.993. The 0.2° C. step is clearly visible in the beat rate, while the 0.1° C. step is at the noise limit. Such sensitivity to temperature further exemplifies the need for a tight control of temperature in cell-based assays.

Experiments aimed at evaluating the stability of the temperature over time were also performed (data not shown). Consistency is usually more important than accuracy with extracellular recordings, as most of the measurements are relative (referred to a baseline activity).

These experimental results clearly highlight the key features of the integrated heating, such as low power dissipation and fast settling times. Most importantly, these features come at a negligible cost, compared to using specialized CMOS circuitry, as discussed above. The spatial localization of the heating also enables multiple, independent arrays to be integrated on the same substrate in a multi-well configuration.

Though flex-MEAs were typically designed for single use only, multiple uses have been performed for longevity studies. Following use, the arrays were cleaned for 60 min in a 5% detergent solution (Contrad® 70, Decon Laboratories, Inc., Bryn Mawr, Pa., USA), rinsed thoroughly in deionized water, sprayed with ethanol, blown dry with nitrogen gas and baked at 65° C. for two hours for complete moisture removal.

Recordings made on flex-MEAs were compared with previous recordings performed on microlithographically defined, glass-based microelectrode arrays (glass-MEAs). These arrays are more representative of conventional MEAs, with smaller and denser electrodes (10 and 22 µm diameter spaced by 100 µm), and more planar surfaces (2 µm silicon nitride passivation). Electrode impedance was in the 100 KΩ range (at 1 kHz) due to electroplating of platinum black. For more information regarding these arrays, please refer to D. A. Borkholder et al. "Microelectrode arrays for stimulation of neural slice preparation," Journal of Neuroscience Methods, 77 (1997), pp. 61-67, which is incorporated herein by reference.

Comparisons were based on multiple signal parameters extracted from baseline activity. The extraction was performed using custom software operating in the Matlab® environment. Six parameters were selected for comparison—amplitude, amplitude ratio, duration, signal-to-noise ratio (SNR), beat rate, and conduction velocity.

Amplitude was defined as the peak-to-peak voltage of each extracellular action potential (AP). Amplitude ratio was defined as the ratio of the amplitude of the two major strokes of the extracellular AP. The duration was defined as the width of the AP downstroke at 50% of its maximum amplitude. The SNR was defined as the ratio of the peak-to-peak amplitude of the AP to the peak-to-peak noise level (six times the standard deviation of the baseline). The local activation time (LAT) reference for each action potential was defined as the point of maximum negative slope of the extracellular AP. The beat rate was then defined as the inverse of the delay between two consecutive LATs. Finally, the conduction velocity was derived using a triangulation method based on the method described by P. V. Bayly et al. in "Estimation of conduction velocity vector fields from epicardial mapping data," IEEE Transactions on Biomedical Engineering, 45, 5 (1998), pp. 563-571, which is incorporated herein by reference.

Ten-second recordings from independent arrays/cultures were randomly selected for each group (10 recordings/group). Electrodes with SNR below 10, as well as occasional outliers detected by visual inspection, were rejected from the parameter extraction step. For each recording, the extracted parameters were averaged over time (10 seconds) and over the available electrodes. Resulting parameters were compared using a one-way ANOVA test (confidence level of 98%), with a multiple comparison test based on Tukey's honestly significant difference criterion.

Table 1 shows a comparison between flex-MEAs and glass-MEAs, bearing smaller, denser electrodes. Mean and standard deviation are given for each parameter.

electrode spacings and electrode sizes are vastly different, and it confirms again the development of a functional, connected syncytium on top of the flex-MEAs. The amplitude of the recorded signals shows an increase with smaller electrodes, with an average strength of 1.41 mV for 10 µm electrodes compared to 0.91 mV for 100 µm electrodes. However, action potential amplitude shows less variation on flex-MEAs, as seen by their lower standard deviation. As a consequence of the signal strengths, SNRs also appear smaller for flex-MEAs (still exceeding 15 on average), but more reproducible.

This comparison shows that flex-MEAs are competitive with conventional MEAs for cardiac cell culture recordings. It also demonstrates that while there is motivation for small electrodes (signal strength, shape reproducibility), large electrodes (up to 100 µm) can provide similarly useful information at a lower cost.

The above experimental results demonstrate the successful extracellular electrical recording based on a practically unmodified, commercial, flexible PCB technology. MEAs manufactured according to the present invention showed consistent biocompatibility, supporting repeated HL-1 cardiomyocyte culture for over three weeks. HL-1 signals were reliably recorded from these arrays and further demonstrated the formation of a functional syncytium, with beating and signal propagation characteristics similar to cultures observed on expensive, conventional, glass-based MEAs. The manufactured MEA devices also incorporated on-chip heating capabilities, demonstrating low-power, fast-response temperature control of the cell culture. The recording of synchronous activity, and furthermore the observation of uniform spreading of the depolarization, shows that the fairly non-planar topography of the flex-MEAs (recessed electrodes) neither prevents the formation of a connected tissue, nor disrupts the signal propagation through the culture.

The use of an unmodified, flex PCB technology presents numerous advantages, including low cost (enabling single use), suitability for scaled-up designs (multi-array substrates), simplified packaging (monolithic device—no assembly necessary except for the culture chamber), straightforward compatibility with chip-on-board assembly (enabling on-chip processing using commercial integrated circuits such as multiplexers), and, as demonstrated herein, integration of on-chip, low-power temperature control systems. In addition, utilizing a commercial channel allows easier access to MEA technology, as the only tool required is a PCB layout editor (freely available through the manufacturers). This new approach also benefits from the current PCB industry's fast turn-around time. Furthermore, due to a con-

TABLE 1

| MEA type | Electrode diameter | Beat Rate [Hz] | Conduction Velocity [cm/s] | AP Amplitude [mV] | AP Stroke Amplitude Ratio | AP Duration [ms] | SNR |
|---|---|---|---|---|---|---|---|
| Glass | 10 µm | 3.40 ± 0.92 | 1.61 ± 0.4 | 1.41 ± 0.82 | 0.46 ± 0.10 | 5.90 ± 1.75 | 22.3 ± 11.7 |
|  | 22 µm | 3.33 ± 0.64 | 1.83 ± 0.6 | 1.29 ± 0.88 | 0.50 ± 0.07 | 5.70 ± 1.45 | 22.4 ± 15.4 |
| Flex | 65 µm | 2.75 ± 0.49 | 1.91 ± 0.7 | 0.95 ± 0.52 | 0.72 ± 0.23 | 6.20 ± 1.75 | 17.0 ± 3.4 |
|  | 100 µm | 3.07 ± 1.19 | 1.91 ± 0.5 | 0.91 ± 0.40 | 0.73 ± 0.24 | 6.02 ± 1.80 | 18.7 ± 3.2 |

It can be seen that the beat rate does not appear significantly different between size and type and does not exhibit any trend, showing the lack of influence of the microelectrode type on the beating properties of the HL-1 cultures. Similarly, no significant difference in the conduction velocity of the depolarization wave is noted. This is remarkable, as the interstant push for denser integration of electronic components at low cost, finer features will likely extend the application of this type of PCB-based, low cost MEAs to neuronal cultures.

Although the present invention and its advantages have been described in detail, it should be understood that drawings, tables, and description disclosed herein illustrate technologies related to the invention, show examples of the invention, and provide examples of using the invention and are not to be construed as limiting the present invention. Known methods, techniques, or systems may be discussed without giving details, so to avoid obscuring the principles of the invention.

As one of ordinary skill in the art will appreciate, the present invention can be implemented, modified, or otherwise altered without departing from the principles and spirit of the present invention. For example, although according to an embodiment of the invention the flex-PCB based MEA device (flex-MEA) is particularly useful for extracellular recording of cardiomyocyte cultures, one skilled in the art will readily recognize that it is within the scope of the present invention to add or modify the printed circuits for extracellular recording of other electrically active cell cultures, stimulation of electrically active or non-active cell cultures, impedance measurement of electrically active or non-active cell cultures, and/or different commercial applications.

Furthermore, the MEA printed circuits can be modified with multiple wells (e.g., 24-, 48-, and 96-well), onboard multiplexer, and other commercially available electronic components such that they can be packaged as low cost disposable cartridges for, e.g., pharmaceutical screening applications.

Similarly, the electrode configuration and properties (e.g., size, plating) can be tailored for different biological tissues, e.g., neuronal cultures, pancreatic cells, guts cells. For example, the electrodes may be configured or arranged as an array of arrays that correspond to and conform with the standard format of multiwell plates such as 24-, 48-, and 96-well-plates.

Accordingly, the scope of the present invention should be determined by the following claims and their legal equivalents.

We claim:

1. A method of fabricating a plurality of microelectrode array (MEA) devices simultaneously, said method comprising:
   providing a substrate; and
   simultaneously defining a plurality of said MEA devices on said substrate utilizing a selected printed circuit board (PCB) fabrication process, wherein each of said plurality of MEA devices having an MEA and at least one sensor, wherein said at least one sensor is an electrode with additionally deposited thereon one or more transduction layers or a non-electrode sensor; wherein
   said substrate is characterized as flexible or rigid; and wherein
   said device is useful for biological applications including recording of electrically active cell cultures, stimulation of electrically active and non-active cell cultures, and impedance measurement of electrically active and non-active cell cultures.

2. The method of claim 1, wherein
said substrate is made of a material selected from the group consisting of polymer, polyimide, liquid crystal polymer, polyester, polyethylene naphtalate, and polytetrafluoroethylene.

3. The method of claim 1, wherein
said substrate contains conductive traces on one or both sides thereof.

4. The method of claim 1, wherein
said sensor is an integrated temperature sensor/heater, a heater, a temperature sensor, a pH sensor, a glucose sensor, a dopamine sensor, an ion selective amperometric sensor, an oxygen sensor, or a combination thereof.

5. The method of claim 1, wherein
said sensor is an integrated temperature sensor and heater; wherein
said temperature sensor is composed of conductive traces for providing a direct and accurate temperature measurement of said substrate; and wherein
said heater is composed of conductive traces for providing low-power heating of said substrate in a controlled manner.

6. The method of claim 1, wherein said defining step further comprises the steps of
defining a set of electrodes as oxygen sensor electrodes;
depositing and patterning a solid electrolyte and a passivation layer on said set of electrodes, thereby integrating an oxygen sensor.

7. The method of claim 1, further comprising the step of applying a plurality of metal layers to integrate features and increase routing density.

8. The method of claim 1, wherein said defining step further comprises the steps of
applying coverlays; and
defining electrodes by laser etching or plasma etching said coverlays.

9. The method of claim 1, wherein said defining step further comprises the steps of
defining openings in coverlays; and
applying said coverlays.

10. The method of claim 1, wherein said substrate contains patterned conductive traces and wherein said substrate is insulated with coverlays, further comprising the step of
defining electrodes using said conductive traces of minimal line width crossed by perpendicular openings in said coverlays having a minimal line width.

11. The method of claim 1, wherein said substrate is insulated with at least one coverlay having an opening through which electrodes are defined, and wherein said defining step further comprises the step of
utilizing a thermal reflow resulting from melting an adhesive layer between said substrate and said coverlay to reduce size of said opening.

12. The method of claim 1, wherein said substrate is insulated with at least one coverlay, and wherein said defining step further comprises the step of
utilizing a single opening in said coverlay to define multiple electrodes with metal lines, each having a minimal width and being exposed at periphery of said opening.

13. The method of claim 1, wherein said defining step further comprises the step of
drilling a single hole through metal lines deposited on a coverlay and laminated to said substrate such that multiple vertical electrodes are defined at bottom and periphery of said hole and are capable of providing intimate contact with cells or biological tissue; wherein size of each of said vertical electrodes is defined by a cross-section of a minimal width metal line.

14. The method of claim 1, further comprising the step of arranging said plurality of MEAs into arrays of MEAs that correspond to a multiwell plate format.

15. The method of claim 14, further comprising the step of integrating a plurality of wells directly onto said substrate via said PCB fabrication process by defining said wells on coverlays prior to laminating said coverlays onto said substrate.

16. The method of claim 15, further comprising the step of enabling said wells to share a common culture media having certain chemical and biochemical conditions, thereby allowing simultaneous experiments on electrically and physically independent cultures under said chemical and biochemical conditions.

17. The method of claim 15, further comprising the step of enabling each of said wells to have an individual culture medium, thereby allowing simultaneous experiments on electrically, physically, and chemically independent cultures.

18. The method of claim 15, further comprising the step of filling or draining overlying fluid, allowing said wells to transition between fluidically coupled wells to fluidically and electrically isolated wells.

19. The method of claim 15, further comprising the step of chemically modifying a top surface of a coverlay to prevent cells from growing on said top surface and connecting adjacent wells.

20. The method of claim 1, further comprising the step of incorporating said device with discrete or integrated circuit electronic components including amplifiers and multiplexers, thereby increasing noise performance and electrode/well density.

21. The method of claim 1, further comprising the step of plating said MEA with a coating having necessary electrical properties for recording electrical signals from, stimulation to, or impedance measurement of said electrically active cell cultures.

22. A method of fabricating a plurality of microelectrode array (MEA) devices simultaneously, each MEA device having an MEA and at least one sensor, said method comprising:
providing a substrate; and
simultaneously defining a plurality of MEAs and sensors on said substrate utilizing a selected printed circuit board (PCB) fabrication process, wherein said defining step comprises the steps of
defining a set of electrodes as oxygen sensor electrodes; and
depositing and patterning a solid electrolyte and a passivation layer on said set of electrodes, thereby integrating an oxygen sensor;
wherein said substrate is characterized as flexible or rigid; and
wherein said device is useful for biological applications including recording of electrically active cell cultures, stimulation of electrically active and non-active cell cultures, and impedance measurement of electrically active and non-active cell cultures.

23. A method of fabricating a plurality of microelectrode array (MEA) devices simultaneously, each MEA device having an MEA and at least one sensor, said method comprising:
providing a substrate;
simultaneously defining a plurality of MEAs and sensors on said substrate utilizing a selected printed circuit board (PCB) fabrication process; and
integrating a plurality of wells directly onto said substrate via said PCB fabrication process by defining said wells on coverlays prior to laminating said coverlays onto said substrate;
wherein said substrate is characterized as flexible or rigid; and
wherein said device is useful for biological applications including recording of electrically active cell cultures, stimulation of electrically active and non-active cell cultures, and impedance measurement of electrically active and non-active cell cultures.

24. The method of claim 23, further comprising the step of enabling said wells to share a common culture media having certain chemical and biochemical conditions, thereby allowing simultaneous experiments on electrically and physically independent cultures under said chemical and biochemical conditions.

25. The method of claim 23, further comprising the step of enabling each of said wells to have an individual culture medium, thereby allowing simultaneous experiments on electrically, physically, and chemically independent cultures.

26. The method of claim 23, further comprising the step of filling or draining overlying fluid, allowing said wells to transition between fluidically coupled wells to fluidically and electrically isolated wells.

27. The method of claim 23, further comprising the step of chemically modifying a top surface of a coverlay to prevent cells from growing on said top surface and connecting adjacent wells.

* * * * *